United States Patent [19]
Womack, Jr. et al.

[11] Patent Number: 5,866,751
[45] Date of Patent: Feb. 2, 1999

[54] ENERGY RECOVERY AND TRANSPORT SYSTEM

[75] Inventors: E. Allen Womack, Jr., New Orleans, La.; Rodger W. McKain, Chagrin Falls; Mary A. Witt, Canton, both of Ohio

[73] Assignee: McDermott Technology, Inc., New Orleans, La.

[21] Appl. No.: 722,732

[22] Filed: Oct. 1, 1996

[51] Int. Cl.⁶ .................................................. C07C 2/00
[52] U.S. Cl. ........................ 585/899; 585/518; 208/108
[58] Field of Search ............................ 208/108; 585/899, 585/518, 14

[56] References Cited

U.S. PATENT DOCUMENTS

| | | | |
|---|---|---|---|
| 1,439,171 | 12/1922 | Kennedy | 208/26 |
| 1,591,735 | 7/1926 | Beattie | 208/17 |
| 1,785,270 | 12/1930 | Lavirotte | 208/20 |
| 2,917,375 | 12/1959 | Hudson | 44/62 |
| 2,956,001 | 10/1960 | Spars et al. | 208/27 |
| 2,981,675 | 4/1961 | Hemminger et al. | 208/95 |
| 3,308,052 | 3/1967 | Ireland et al. | 208/27 |
| 3,346,498 | 10/1967 | de Vries | 252/59 |
| 3,445,205 | 5/1969 | Patinkin et al. | 44/62 |
| 3,548,846 | 12/1970 | Allen | 137/13 |
| 3,576,735 | 4/1971 | Murphy, Jr. et al. | 208/27 |
| 3,804,752 | 4/1974 | Merrill, Jr. et al. | 208/370 |
| 3,821,104 | 6/1974 | Hughes et al. | 208/93 |
| 4,010,622 | 3/1977 | Etter | 62/48 |
| 4,125,566 | 11/1978 | Trin Dinh et al. | 260/676 R |
| 4,628,133 | 12/1986 | Minderhoud et al. | 585/310 |
| 4,727,205 | 2/1988 | Veleyi et al. | 585/407 |
| 4,727,207 | 2/1988 | Paparizos et al. | 585/415 |
| 4,755,230 | 7/1988 | Ashton et al. | 134/22.14 |
| 4,832,819 | 5/1989 | Hamner | 208/27 |
| 4,950,821 | 8/1990 | Ratnasamy et al. | 585/310 |
| 5,015,799 | 5/1991 | Walker et al. | 585/500 |
| 5,223,122 | 6/1993 | Katayama | 208/24 |

OTHER PUBLICATIONS

Wechem at al., "The Shell Middle Distillate Synthesis Process", Date Unknown, but apparently pre–1993, pp. 553–559. no date.

"Shell plans natural gas to oil products plant in Malaysia", *Process Engineering*, Sep. 1989, p. 21.

Mack, "Bring know–how, bring money", *Forbes*, Jul. 4, 1994, pp. 42–43.

Sie et al., "Conversion of Natural Gas to Transportation Fuels via the Shell Middle Distillate Synthesis Process (SMDS)", *Catalysis Today*,8, 1991, pp. 371–394. no month.

Burgt et al., "The Shell Middle Distillate Synthesis Process", in D.M. Bibby and co–workers, eds. *Methane Conversion*, Elsevier Science, Inc., New York, 1988, pp. 473–482. no month.

*Encyclopedia of Energy Technology and the Environment*, Vol. 3, John Wiley & Sons, Inc., New York, 1995, pp. 2254–2255. no month.

*Encyclopedia of Chemical Technology*, Third Edition, Vol. 24, John Wiley & Sons, Inc., New York, 1984 pp. 466–479. no month.

*Perry's Chemical Engineers' Handbook*, Sixth Edition, McGraw–Hill book Company, New York, 1984, pp. 9–35–9–36. no month.

(List continued on next page.)

*Primary Examiner*—Walter D. Griffin
*Assistant Examiner*—Nadine Preisch
*Attorney, Agent, or Firm*—R. J. Edwards; Eric Marich

[57] ABSTRACT

A safe, environmentally sound method for transporting energy-containing hydrocarbons from a remote natural gas source of hydrocarbons to a local site for further processing or refining. The natural gas is converted at the remote site, using a modified Fischer-Tropsch process, to produce non-volatile, long chain hydrocarbons, i.e., paraffins ($C_{20}$–$C_{36}$) at the remote site, transporting the paraffins via rail, ship, or cargo air plane to a local site, and then further processing and/or refining the paraffins via distillation, cracking, or combining with other hydrocarbon feedstocks to produce fuel products at the local site for use.

17 Claims, 3 Drawing Sheets

OTHER PUBLICATIONS

*Encyclopedia of Energy Technology and the Environment,* Vol. 2, John Wiley & Sons, Inc., 1995, pp. 1520–1526. no month.

DIALOG® computer database search result–Abstract of "Carbon: hydrogen carrier or disappearing skelton?"by DeJong, K.P. and Van Wechem, H.M.H., found in *International Journal of Hydrogen Energy,* Vol. 20, No. 6, Jun. 6, 1995, pp. 493–499, one paragraph Abstract.

DIALOG® computer database search result –Abstract of "Shell Middle Distillate Synthesis:The process, the products, the plant"$_{14}$ by Tijm, P.J.A., paper presented at the American Chemical Society national meeting, Washington, DC Aug. 21–26, 1994 publication date 1994 in *Fuel 87* at page 639, one paragraph Abstract.

DIALOG® computer database search result–Abstract of technical paper concerning "Conversion of natural gas to transportation fuels via the Shell Middle Distillate Synthesis Process (SMDS)", by Van Wechem, H.M.H., Senden, M.M.G., and Tijm, P.J.A., presented at 14$^{th}$ World Petroleum Congress, (Stavanger, Norway, May 29–Jun. 1, 1994), Conference. Proceedings vol. 3, p.263, 1994, one paragraph Abstract.

DIALOG® computer database search result–Abstract of "Conversion of natural gas to clean transportation fuels: The Shell Middle Distillate Synthesis Process (SMDS)"by Ansorge, J. and Hoek, A., presented at the symposium on Octane and Cetane Enhancement Processes for Reduced–Emissions Motor Fuels, San Francisco, California, Apr. 5–10, 1992, published in Preprints –Division of Petroleum Chemistry, American Chemical Society, vol. 37, No.3, at p. 832, 1992, one paragraph Abstract.

DIALOG® computer database search result–Article entitled "Malaysia–The Partners", *APS Review Gas Market Trends,* Jul. 4, 1994, vol. 42, No. 26. Publisher Arab Press Service Organisation.

DIALOG® computer database search result–Article entitled "Shell MDS ships historic cargo", *International Gas Reort,* Oct. 15, 1993. Publisher Financial Times Business Information Ltd.

DIALOG® computer database search result –Article entitled "Plentiful natural gas headed for big growth in Mideast", by S.H. Hamid et al., *Oil and Gas Journal,* Vol. 93, No. 4, p. 51, Jan. 23, 1995.

DIALOG® computer database search result –Article entitled "Natural gas conversion technologies", by G.J. Stiegel et al., *Chemistry and Industry,* No. 21, p 854, Nov. 7, 1994.

DIALOG® computer database search result –Article entitled "Shell's gas to middle distillates plant back on line", *Oil and Gas Journal,* Vol. 91, No. 43, p. 30, Oct. 25, 1993.

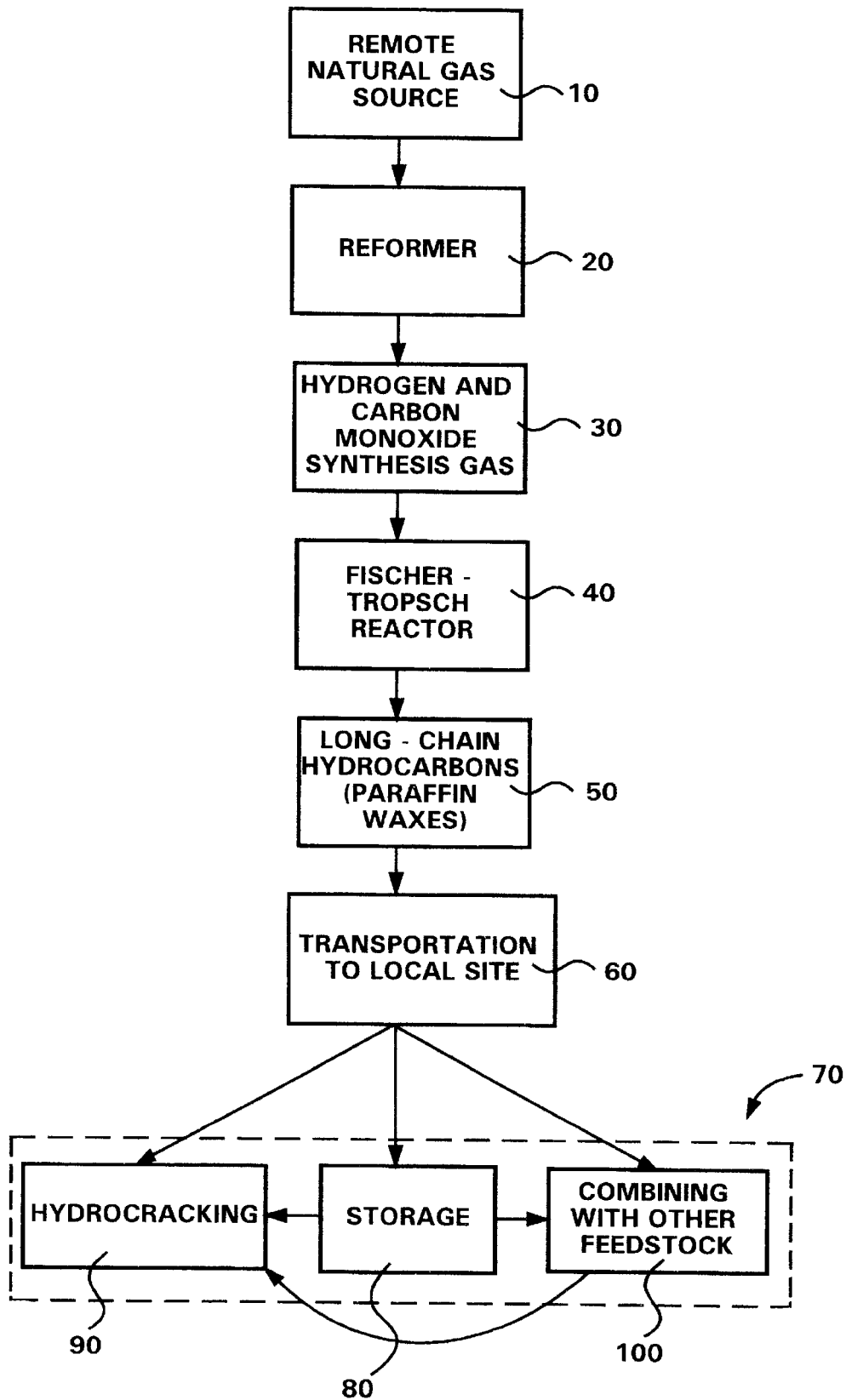

5,866,751

ENERGY RECOVERY AND TRANSPORT SYSTEM

FIELD AND BACKGROUND OF THE INVENTION

The present invention relates generally to the task of providing fossil fuel energy sources from a remote location to a local site for use. In particular, the present invention is drawn to a safe, environmentally sound method for transporting hydrocarbons from their remote, natural points of origin to local sites so that the energy content of such fuels can be used. More particularly, the present invention is drawn to a method of converting natural gas at a remote site, using a modified Fischer-Tropsch process, to produce non-volatile, long chain hydrocarbons, i.e., paraffins ($C_{20}$–$C_{36}$) at the remote site, transporting the paraffins via rail, ship, or cargo air plane to a local site, and then further processing and/or refining the paraffins via distillation, cracking, or combining with other hydrocarbon feedstocks to produce fuel products at the local site for use.

Current methods for transporting certain hydrocarbon fuels via land or across the oceans present certain health hazards and environmental dangers.

Crude oil and refined fuel oil are commonly transported between continents by supertankers holding millions of gallons. Even with segmented tanks and double hull construction, unnatural disasters can occur when, due to human error or natural forces, the supertankers used to transport the oil are damaged.

In February 1996, an oil tanker ran aground off the coast of Wales in an environmentally endangered area, spilling several hundred thousand gallons of oil into the Atlantic Ocean.

The EXXON VALDEZ spill off of the coast of Alaska is one of the most vivid examples of the devastating effect that spilled fuels can have on the environment. Years following the disaster, the coastline was still being cleaned and the ecologies are still recovering as best they can.

Huge reserves of natural gas are found in many regions of the world, but they are frequently located in remote areas far from the actual centers of consumption. Traditional pipeline costs can account for as much as one-third of the total natural gas cost. Thus, there are tremendous strategic and economic incentives to provide on-site gas conversion to liquids.

Liquefied natural gas is another common fuel that is transported through tankers, trucks and pipelines and stored in large capacity tanks. In order to more efficiently transport and store natural gas, it is liquefied by reducing its pressure and temperature. Liquefied natural gas explodes easily, and it must be kept refrigerated and pressurized to remain liquefied. Any accidental leak of liquefied natural gas instantly begins to boil, gaining heat from the surrounding air, ground, building, or from whatever it may come into contact.

Natural gas is a combination of highly flammable hydrocarbon gases. Natural gas is normally composed of about 80% to 95% methane. When liquefied natural gas boils, as during a leak, it becomes even more volatile, and subject to rapid ignition and explosion from the slightest spark.

Liquefied natural gas poses even greater difficulties and dangers to the people and ecologies where it is stored and transported than crude oil. Precautions are taken to avoid explosions and fires, but disasters involving liquefied natural gas have been documented.

For example, in October 1944, a liquefied natural gas storage facility burst, releasing 2 million gallons of liquefied gas into streets and sewers of Cleveland, Ohio. The gas was easily ignited, burned and exploded, killing 131 people and razing 29 acres of developed property.

In February 1973, a liquefied natural gas tank on Staten Island, N.Y. exploded, killing 40 people. A pipeline at the same facility exploded in 1994.

A liquefied natural gas explosion occurred while workers were loading fuel trucks at a Hammond, Ind. site in February 1990. Two people were killed, several others were injured and the town was evacuated.

It is thus reasonable to seek transport methods for fossil fuels which are less vulnerable to danger.

However, it is generally accepted in the fuel production and refining industry that refining processes for fossil fuels should work to maximize the usable end product fraction at nearly every stage.

As discussed in *The Encyclopedia of Energy Technology and the Environment*, Vol. 2, under the main topic "Fuels, Synthetic, Liquid", at page 1520 et seq., the huge resources of natural gas have been recognized to be a source for conversion to liquid fuels as well. In general, the proven technology to upgrade methane, the main component of natural gas, is via steam reforming to produce synthesis gas, $CO+H_2$. Such a gas mixture is clean and when converted to liquids produces fuels substantially free of heteroatoms such as sulfur and nitrogen. There are pathways from a synthesis gas which can be taken, and which have been commercialized, to produce liquid fuels from natural gas. One such pathway involves coupling with Fischer-Tropsch technology to produce fuel range hydrocarbons directly or upon further processing.

For instance, a SHELL OIL process, parts of which are described in U.S. Pat. Nos. 4,587,008 and 4,628,133 to Minderhoud et al., and more fully described in the September 1989 issue of *Process Engineering* at page 21, involves modifying a Fischer-Tropsch process to produce heavy paraffins at an intermediate stage from natural gas. The purpose of this modification is to improve the end product resulting from further processing of the paraffins, by eliminating the formation of certain undesirable length hydrocarbon chains.

Referring to FIG. 1, there is shown a schematic illustration of the Shell Middle Distillate Synthesis (SMDS) process developed by Shell Oil Company, which uses remote natural gas as the feedstock. FIG. 1 shows a simplified flow scheme. The two-step process involves Fischer-Tropsch synthesis of paraffinic wax called the heavy paraffin synthesis (HPS). The wax is subsequently hydrocracked and hydroisomerized to yield a middle distillate boiling range product in the heavy paraffin conversion (HPC). In the HPS stage, wax is maximized by using a proprietary catalyst having high selectivity toward heavy products and by the use of a tubular, fixed-bed Arge-type reactor. The HPC stage employs a commercial hydrocracking catalyst in a trickle flow reactor. The effect of hydrocracking the light paraffins is shown in FIGS. 2 and 3. As shown in FIG. 2, the product composition as a function of carbon number for the Shell Middle Distillate Synthesis process following HPS is much broader than what is obtained after the HPC step. The HPC step allows for production of a narrower range of hydrocarbons which is generally not possible with conventional Fischer-Tropsch technology. This aspect is shown in FIG. 3. Shell's two-step SMDS technology allows for process flexibility and varied product slates. The liquid product obtained consists of naphtha, kerosene and gas oil in ratios of from 15:25:60 to 25:50:25, depending on process conditions. High quality gas oil and kerosene are obtained. The products manufactured are predominantly paraffinic, free from sulfur, nitrogen and other impurities and have excellent combustion properties. The SMDS process has also been proposed to produce chemical intermediates, paraffinic sulfas, and extra high viscosity index (XHVI) lubeoils.

However, there is no teaching that producing heavy paraffins as an end product is beneficial, or that stopping the process after producing heavy paraffin is beneficial. The heavy paraffins, or wax products, produced by the modified Fischer-Tropsch synthesis process are instead immediately refined as part of a continuous process at the same location to produce middle distillate fuel oils which are low in methane and ethane content. These middle distillate fuel oils have a much greater economic value than the paraffins produced during the process and are therefore more desirable to produce as an end product. These middle distillates are also more flammable and cause more environmental damage when they are spilled.

Paraffin wax, by comparison, is non-volatile, floats on water and does not disperse or boil from its solid form at ambient temperatures. It is also considered to be of less economic value and to have few end uses as fuel. The SHELL process is the only one in the fuel production industry which considers the synthesis of paraffins to be beneficial, but solely for the purpose of further refining the paraffins in a continuing process to produce greater quantities of gasoline more efficiently.

As taught by U.S. Pat. Nos. 1,439,171, and 4,125,566, and others, heavy paraffins produced by distillation and Fischer-Tropsch synthesis are considered undesirable by-products of these fuel production processes.

Paraffin wax is simply a longer straight hydrocarbon chain than natural gas, (the shortest chains) and oils (middle length chains). Paraffin wax can be distilled to produce natural gases and oils, or added to other feedstocks to enrich the amount of hydrocarbons present or improve the quality of the refined oil. However, heavy paraffins have little use as a fuel without further refining.

Waxes alone are never transported from remote locations closer to local end user sites for fuel production refining. Paraffin waxes have been disclosed to be combined with oils and pumped through pipelines, as in U.S. Pat. Nos. 3,458, 846 and 3,804,752. Paraffin waxes are also taught to be combined or recombined with local feedstocks to improve the quality of the end product, such as in U.S. Pat. Nos. 3,821,104, 3,308,052 and 2,917,375. Waxes used in these processes are often the by-products created in the initial refining.

SUMMARY OF THE INVENTION

It is a primary object of this method to minimize and avoid many of the dangers presented by the transport and storage of fuels prior to transport and use.

Accordingly, a method is disclosed whereby a natural gas source at a remote site is provided to an apparatus for synthesizing long-chain hydrocarbons having a solid form at ambient temperatures. The straight, long-chain hydrocarbons, or heavy paraffin waxes, are then transported to a local site for storage, hydrocracking, distillation to usable fuels, or mixing with local feedstocks prior to distillation to produce usable fuels.

The natural gas source may be in a remote part of the world, with little use for the fuel at that location. The apparatus for synthesizing the long-chain hydrocarbons is located proximate to the gas source and can be a reformer for creating hydrogen and carbon monoxide synthesis gases from the natural gas.

The synthesis gases are next provided to a Fischer-Tropsch reactor. The Fischer-Tropsch reactor utilizes an appropriate catalyst for generating almost exclusively straight long-chain hydrocarbons, preferably heavy paraffin waxes, from the synthesis gases.

No further distilling, reacting or refining of the heavy paraffin waxes is conducted at the remote gas source location.

The waxes in solid form are then loaded aboard known means of transport, such as ships or trucks, and moved to a local site. The waxes may be stored, and/or refined to usable fuels, at the local site.

By intentionally producing heavy paraffin wax products from the natural gas synthesis, and then terminating the refining process until after the hydrocarbons have been transported to a local site nearer to the end use, many of the dangers of transporting crude and refined fuel oil and liquefied natural gas are avoided.

No additional handling or treatment of the heavy paraffin waxes is required to maintain the wax in solid form for transport, as the paraffin wax is normally a solid at ambient temperatures. The paraffin wax is non-volatile, and will not explode or boil upon contact with air, like liquefied natural gas. Paraffin wax floats on water, and does not diffuse or disperse like oil, making it much easier to retrieve and clean in the event of an accident resulting in the wax being dislodged from the transport.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWINGS

In the drawings:

FIG. 4 is a flow chart showing the steps of the method according to the present invention.

DESCRIPTION OF THE PREFERRED EMBODIMENTS

Figure 1:
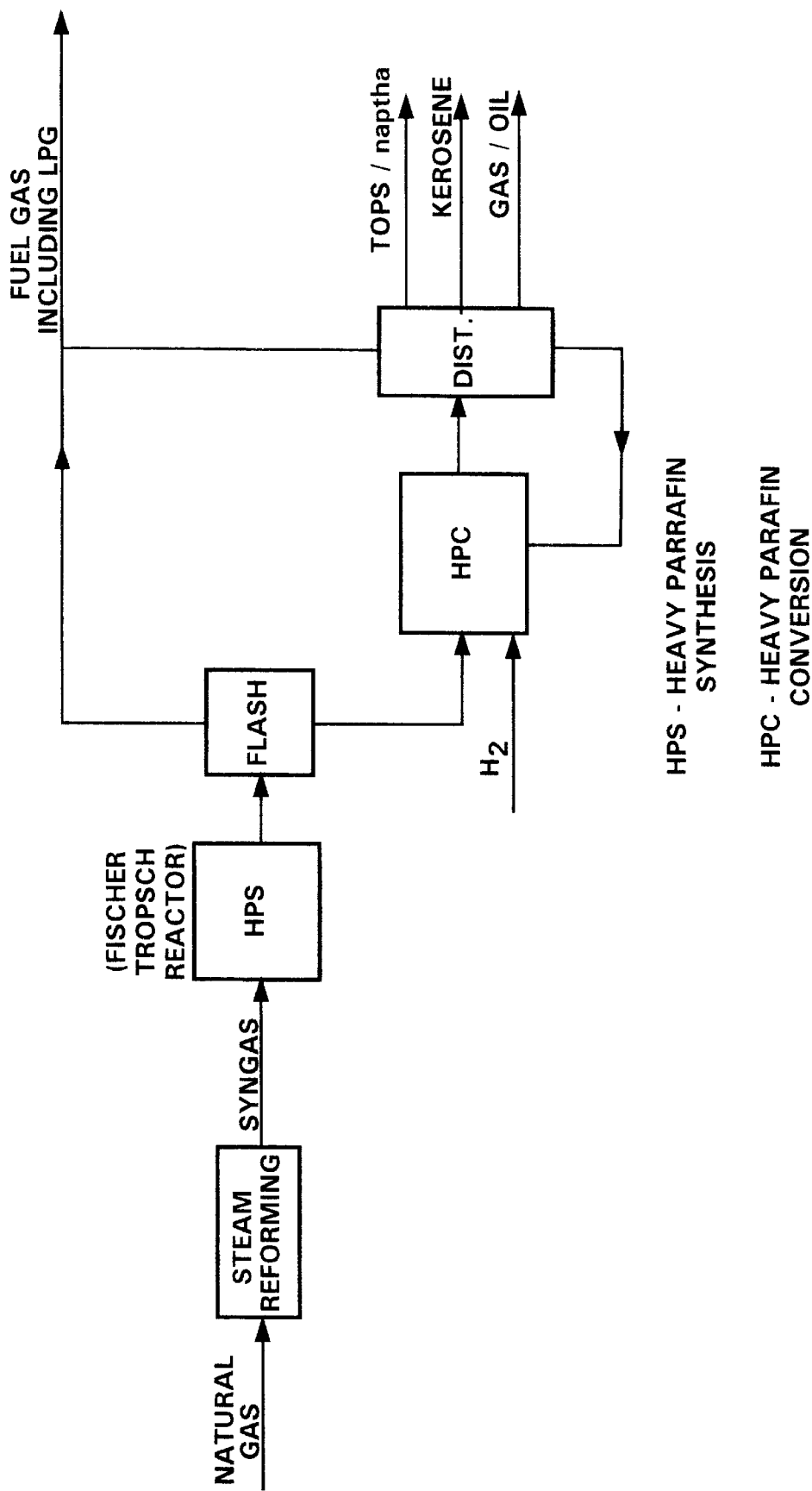
FIG. 1 is a schematic representation of the Shell Middle Distillate Synthesis (SMDS) process.
Figure 2:
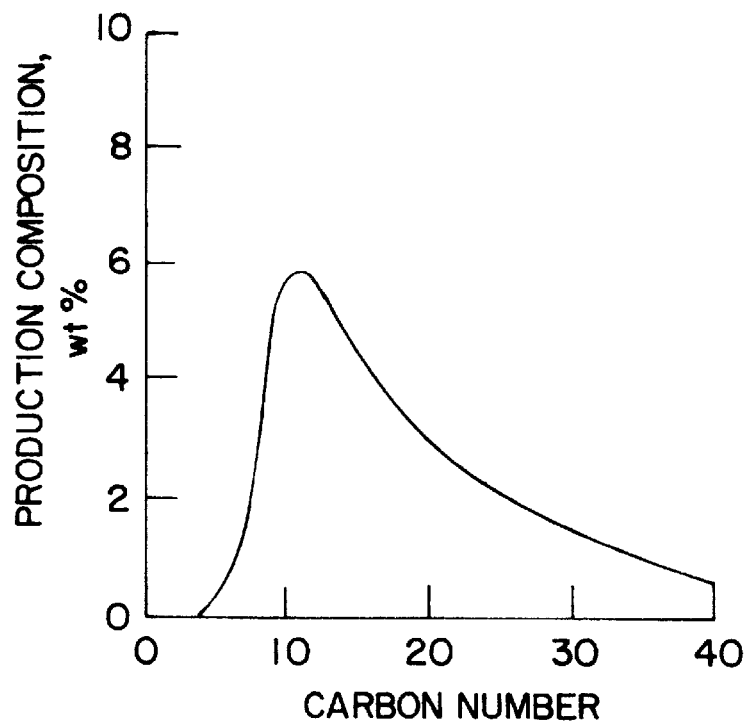
FIG. 2 is a graphical representation of production composition versus carbon number following the HPS stage of FIG. 1.
Figure 3:
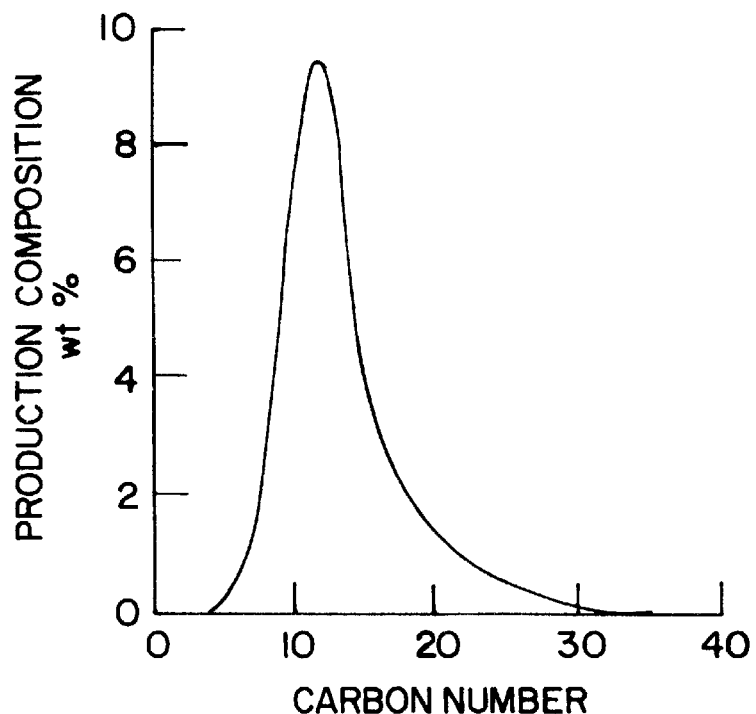
FIG. 3 is a graphical representation of production composition versus carbon number following the HPC stage of FIG. 1.

Referring now to FIG. 4, there is shown a flow chart of the steps of the method according to the present invention. A natural gas source 10, which is located in a remote site, is provided to a reformer 20 to produce synthesis gases 30. The synthesis gases 30 consist primarily of hydrogen and carbon monoxide gases. The reformer 20 is also at the remote site, and preferably in close proximity to the natural gas source 10.

The synthesis gases 30 are then converted within Fischer-Tropsch reactor 40 to produce straight long-chain hydrocarbons, or heavy paraffin waxes 50, at the remote site.

As used herein, the term paraffin wax is defined to be a petroleum wax consisting principally of normal alkanes, and which is microcrystalline, brittle, and comprised of 40–90 wt. % normal paraffins with the remainder $C_{18}$–$C_{36}$ isoalkanes and cycloalkanes. Typical physical properties of such paraffin waxes are as set forth in Table 1 below.

TABLE 1

Physical Properties of Paraffin Wax

| | |
|---|---|
| Flash point, °C. | 204, min |
| Viscosity at 98.9° C., mm²/s (SUs) | 4.2–7.4 (40–50) |
| Melting range, °C. | 46–68 |
| Refractive Index at 98.9° C. | 1.430–1.433 |
| Average Mol. Wt. | 350–420 |
| Carbon atoms per molecule | 20–36 |
| Other physical aspects | friable to crystalline |

The heavy paraffin waxes 50 are naturally in solid form, and can be easily loaded and transported 60 to a second, local site 70. The local site 70 may have facilities for storage 80, hydrocracking 90, or combining the paraffin wax with other local feedstocks 100. Alternatively, the local site 70 may have a combination of one or more of these facilities 80, 90, 100.

The natural gas source 10 may be a gas well, either on land or on an ocean platform, especially one which is distant from the place where the end use will occur.

The reformer 20 may be a reactor having catalyst-filled tubes located in a firebox. The natural gas 10 is fed through the tubes, where it is converted to the hydrogen and carbon monoxide gases 30.

The Fischer-Tropsch reactor 40 has a chamber containing molten wax and a catalyst forming a slurry. The hydrogen and carbon monoxide gases 30 are bubbled through the slurry, forming hydrocarbon chains. The Fischer-Tropsch reactor 40 has a mechanism which is conducive to long-chain hydrocarbon growth that is not selective to particular boiling ranges. An appropriate catalyst can be selected to maximize the formation of heavy paraffins 50, and other Fischer-Tropsch process parameters such as pressure, temperature, and residence time can also be varied to emphasize the formation of such heavy paraffin waxes in the $C_{20}$–$C_{36}$ range. The resulting heavy paraffins 50 are straight long-chain hydrocarbons which can be hydrocracked into jet fuels, gasoline and other middle distillate fuel products at a later, more appropriate time.

After transportation 60 to the local site, the long-chain paraffin wax hydrocarbons can be stored 80, further hydrocracked 90, or combined with other feedstock 100. This latter aspect depends in large part upon the nature of the hydrocarbon feedstock that would be combined with the long-chain paraffin wax hydrocarbon 50. If the hydrocarbon feedstock is a crude oil, one needs to consider the fact that crude oils differ appreciably in their properties according to origin and the ratio of the different components in the mixture. A typical analysis of some crude oils is set forth below in Table 2.

TABLE 2

Typical analysis of some crude oils

| | Arab Extra Light* | Alameen Egypt | Arab Heavy | Bakr-9 Egypt |
|---|---|---|---|---|
| Gravity, °API | 38.5 | 33.4 | 28.0 | 20.9 |
| Carbon residue (wt %) | 2.0 | 5.1 | 6.8 | 11.7 |
| Sulfur content (wt %) | 1.1 | 0.86 | 2.8 | 3.8 |
| Nitrogen content (wt %) | 0.04 | 0.12 | 0.15 | — |
| Ash content (wt %) | 0.002 | 0.004 | 0.012 | 0.04 |
| Iron (ppm) | 0.4 | 0.0 | 1.0 | — |
| Nickel (ppm) | 0.6 | 0.0 | 9.0 | 108 |
| Vanadium (ppm) | 2.2 | 15 | 40.0 | 150 |
| Pour point (°F.) | ≈Zero | 35 | −11.0 | 55 |
| Paraffin wax content (wt %) | — | 3.3 | — | — |

*Ali, M. F. et al. Hydrocarbon Processing, Vol. 64, No. 2, 1985 p. 83.

As indicated by Table 2 above, a typical analysis of some crude oils such as Arab Extra Light characterizes it as a very light oil yielding light and middle distillates while Bakr-9 Egypt oil is considered a heavy oil with many impurities. Using the American Petroleum Institute (API) measurement of gravity, a low API gravity such as the Bakr-9 crude is a case of heavier crude, while a higher API gravity means a lighter crude or product.

Another aspect that needs to be considered if the long-chain paraffin wax hydrocarbons 50 are to be combined with other feedstocks 100, is the maximum allowable wax content for various refineries, and the impact that wax could have on refinery operations. Limited studies have been reported on the solubility behavior of waxes in undefined mixtures; i.e., in petroleum fractions, crude oil, and in kerosene. However, the long-chain paraffin wax hydrocarbon produced from the Fischer-Tropsch process has been defined as an excellent feed for hydrocracking to product middle distillates like diesel and jet fuel. With regard to the solubility of wax in some undefined mixtures, it is important to consider that crude oils differ appreciably in their properties according to origin and the ratio of the different components in the mixture as described above. Long-chain paraffin wax hydrocarbons 50 having a typical melting point of 108° F. are soluble in various base oils depending upon the relationships between the oil type, the temperature in the concentration of paraffin to oil, as measured by weight. In Arab Extra Light, for example, the temperature-to-wax content correlation range for the solubility of paraffin wax in oil is 41° F./2.5% wt. to 115° F./50% wt. In Arab Heavy Oil the range is 64° F./2.5% wt to 131° F./50% wt. Since both of these oil types are typical feedstocks for refineries, it can be concluded that the use of long-chain paraffin hydrocarbons 50 as refinery feedstock additive can be used with the parameters of the ranges set forth above. These parameters are common in refinery operations.

With respect to the modifications of the Fischer-Tropsch process at the remote site to yield more paraffins, it must be remembered that the Fischer-Tropsch mechanism can be considered a polymerization reaction, or more simply, the combining of smaller molecules to make larger molecules, the small molecules of monomers being a $C_1$ species derived from carbon monoxide. This polymerization follows an Anderson-Schulz-Flory (ASF) distribution of molecular weights. Under the assumptions of this model, the entire product distribution is determined by one parameter, namely the probability of the addition of a carbon atom to a chain. When the probability of an addition of a carbon atom is high, and the degree of polymerization is high the resulting Fischer-Tropsch yield is primarily paraffin wax. The probability of the addition of carbon atom is dependent upon the catalyst used. For example, the use of one known Mobil® catalyst identified as CT256-13 consisting of iron, copper, potassium, and oxygen results in a 59.9% paraffin wax yield, which can easily be upgraded via conventional processes into a high quality diesel fuel. Other examples of iron catalysts are known and can be used to produce high yields of higher hydrocarbons and are described in the *Oil Gas European Magazine,* Jan. 1, 1995, at page 19–24.

The heavy paraffins 50 are non-volatile and in a solid form, and can be easily loaded onto boats, trucks, or even cargo airplanes, to transport 60 the wax 50 to the local site 70. The particular method of transport 60 selected does not require special refrigeration, pressurization or flame retardation measures beyond those required for other non-volatile cargoes.

In the event of an accident resulting in the spill of the heavy paraffins 50, they are easier to contain and retrieve than either liquefied natural gas, which often explodes and burns, and oil, which forms large mobile slicks on the ocean or ground. In contrast, the paraffin wax 50 will not easily disperse, diffuse or burn.

Additionally, the solid paraffin wax 50 can be transported with supertankers more economically and efficiently than liquefied natural gas and oil. Transporting liquefied natural gas requires liquefication and regasification plants at each transport terminal. The cost of a reformer 20 and Fischer-Tropsch reactor 40 system at a remote site is less than that of a liquefication plant. As a result, the present method allows the exploitation of natural gas sources 10 considered too remote to be useful, since the cost for extracting and transporting the natural gas 10 is lowered, and the safety of transporting 60 the wax 50 eliminates many environmental concerns.

While a specific embodiment of the invention has been shown and described in detail to illustrate the application of the principles of the invention, it will be understood that the invention may be embodied otherwise without departing from such principles.

We claim:

1. A method for transporting the energy content of a natural gas hydrocarbon fuel from a remote site of origin to a local site for use by converting the natural gas hydrocarbon fuel at the remote site into a non-volatile, solid form which floats on water, will not explode or boil upon contact with air in the same manner as liquid natural gas, and which does not diffuse or disperse like oil, such that it can be transported in solid form in a manner that is non-reactive, non-explosive, and non-toxic with the surrounding environment from the remote site to the local site, and then recovering the energy content of the natural gas hydrocarbon fuel at the local site to produce a useful fuel product, comprising the steps of:

providing natural gas from a source at a remote site of origin;

at the remote site, converting the natural gas into and maximizing the production of long-chain, non-volatile, solid paraffin wax hydrocarbons in the $C_{20}$–$C_{36}$ range;

transporting the long-chain, non-volatile, solid paraffin wax hydrocarbons in solid form from the remote site to a local site; and at the local site, one of storing, hydrocracking, and combining the long-chain paraffin wax hydrocarbons with a feedstock, to recover the energy content of the long-chain paraffin wax hydrocarbons to produce a useful fuel product.

2. The method according to claim 1, wherein the natural gas hydrocarbon fuel at the remote site comprises methane.

3. The method according to claim 1, wherein the step of converting the natural gas hydrocarbon fuel comprises providing the natural gas to a reformer for producing hydrogen and carbon monoxide synthesis gas, and reacting the hydrogen and carbon monoxide synthesis gas to produce the long-chain paraffin wax hydrocarbons.

4. The method according to claim 3, wherein the hydrogen and carbon monoxide synthesis gas is reacted in a Fischer-Tropsch reactor.

5. The method according to claim 4, further comprising the step of selecting a catalyst to maximize the production of long-chain paraffin wax hydrocarbons in the $C_{20}$–$C_{36}$ range in the Fischer-Tropsch reactor.

6. The method according to claim 5, further comprising the step of transporting the long-chain paraffin wax hydrocarbons from the remote site to the local site with a ship.

7. The method according to claim 5, further comprising the step of transporting the long-chain paraffin wax hydrocarbons from the remote site to the local site with a truck.

8. The method according to claim 5, further comprising the step of transporting the long-chain paraffin wax hydrocarbons from the remote site to the local site with a railroad car.

9. The method according to claim 5, further comprising the step of transporting the long-chain paraffin wax hydrocarbons from the remote site to the local site with a cargo airplane.

10. The method according to claim 1, further comprising the step of storing the long-chain paraffin wax hydrocarbons at the local site.

11. The method according to claim 10, further comprising the step of hydrocracking the stored long-chain paraffin wax hydrocarbons at the local site.

12. The method according to claim 10, further comprising combining the stored long-chain paraffin wax hydrocarbons with feedstock at the local site.

13. A method according to claim 12, further comprising the step of hydrocracking the combined stored long-chain paraffin wax hydrocarbons and feedstock at the local site.

14. The method according to claim 4, further comprising the step of varying Fischer-Tropsch process parameters to maximize the production of long-chain paraffin wax hydrocarbons in the $C_{20}$–$C_{36}$ range in the Fischer-Tropsch reactor.

15. The method according to claim 14, wherein said Fischer-Tropsch process parameters comprise at least one of pressure, temperature and residence time.

16. The method according to claim 1, wherein the feedstock is a hydrocarbon feedstock.

17. The method according to claim 16, wherein the hydrocarbon feedstock is crude oil.

* * * * *